United States Patent [19]
Attridge

[11] Patent Number: 5,369,717
[45] Date of Patent: Nov. 29, 1994

[54] OPTICAL WAVEGUIDE ASSAY UNIT AND METHOD OF IMPROVING ASSAY SENSITIVITY USING SAME

[75] Inventor: John W. Attridge, Weybridge, United Kingdom

[73] Assignee: Applied Research System Ars Holding N.V., Netherlands Antilles

[21] Appl. No.: 930,690

[22] PCT Filed: Apr. 10, 1991

[86] PCT No.: PCT/GB91/00567

§ 371 Date: Oct. 5, 1992

§ 102(e) Date: Oct. 5, 1992

[87] PCT Pub. No.: WO91/15751

PCT Pub. Date: Oct. 17, 1991

[30] Foreign Application Priority Data

Apr. 11, 1990 [GB] United Kingdom ............ 9008261.1

[51] Int. Cl.$^5$ .................... G02B 6/00; B01L 9/00; G01N 21/76; G01N 21/01
[52] U.S. Cl. .................................. 385/12; 385/27; 385/31; 385/38; 385/129; 422/100; 422/104; 436/164; 436/172; 436/804; 356/244; 356/246; 250/227.25; 250/458.1; 250/459.1

[58] Field of Search .................... 385/31, 147, 12, 27, 385/38, 14, 129, 130, 131, 132; 422/100, 102, 103, 104, 112, 115; 436/164, 165, 169, 170, 172, 805; 356/244, 256; 606/1, 2, 10, 13; 250/227.11, 227.14, 277.25, 458.1, 459.1

[56] References Cited

U.S. PATENT DOCUMENTS

| 4,124,364 | 11/1978 | Dalgoutte | 565/4.21 |
| 4,469,500 | 9/1984 | Miller | 65/112 |
| 5,061,857 | 10/1991 | Thompson et al. | 250/458.1 |
| 5,166,515 | 11/1992 | Attridge | 250/227.25 |
| 5,186,897 | 2/1993 | Eason et al. | 422/100 |
| 5,192,502 | 3/1993 | Attridge et al. | 422/57 |
| 5,192,510 | 3/1993 | Zoha et al. | 422/82.05 |
| 5,300,423 | 4/1994 | Zoha et al. | 435/7.1 |

FOREIGN PATENT DOCUMENTS

| 8706956 | 11/1987 | WIPO | 385/12 X |
| 8801376 | 2/1988 | WIPO | 385/12 X |
| 9001157 | 2/1990 | WIPO | 385/12 X |

*Primary Examiner*—Brian Healy
*Attorney, Agent, or Firm*—Ostrolenk, Faber, Gerb & Soffen

[57] ABSTRACT

The invention relates to a method of reducing scattering of light emerging from an optical edge of an optical waveguide. According to the invention, the optical edge is maintained in intimate contact with an index matching substance which itself also forms or intimately contacts a further optical component. The invention also relates to a disposable holder suitable for use in the method.

8 Claims, 1 Drawing Sheet

OPTICAL WAVEGUIDE ASSAY UNIT AND METHOD OF IMPROVING ASSAY SENSITIVITY USING SAME

BACKGROUND OF THE INVENTION

The present invention relates to a method of improving the sensitivity of optical assays wherein the light signal to be analyzed emerges from the edge of an optical waveguide. The invention is particularly applicable to assays carried out using fluorescence capillary fill devices (FCFD's) in which an optical waveguide forms one plate of the device.

FCFD's and methods for their manufacture are described in detail in EP-A-171148, whilst photometric methods including assays carried out using FCFD's are described in EP-A-170376.

Assays involving FCFD's rely on angular separation, in light emerging from the optical waveguide, between fluorescence originating from molecules in sample liquid within the FCFD cavity and fluorescence originating from molecules bound, directly or indirectly, to the waveguide. This angular separation occurs because fluorescent material in solution can only fluoresce into the waveguide at relatively large angles relative to the plane of the waveguide since the angle of any incident beam relative to this plane will be increased by refraction at the solution/waveguide interface. Such light consequently emerges from the waveguide at large angles (e.g. >47° relative to the axis of the waveguide). Fluorescent material bound to the surface of the waveguide, on the other hand, emits light into the waveguide at all angles, which light thereafter emerges from the waveguide over a wide range of angles relative to the axis of the waveguide. Thus, by measuring the intensity of fluorescent light emerging from the waveguide at relatively small angles to the axis of the guide (e.g. ≦45° to the axis), it is possible to assess the quantity of fluorescent material bound to the surface of the waveguide since the fluorescent light output in this angular zone is substantially free from fluorescence arising from fluorescent material in solution.

As described in EP-A-171148, a convenient method of manufacturing FCFD's involves preparation of coated glass 'sandwiches' from which individual FCFD's are separated by scribing and breaking. This manufacturing process permits the inexpensive bulk production of FCFD's, this being particularly desirable in view of the disposable nature of these devices.

It is difficult within the context of such a bulk production process, however, to design scribing and breaking procedures which consistently produce FCFD's in which the end of the waveguide from which emerging light is detected (hereinafter referred to as "the optical edge") is optically smooth. It will be appreciated that surface irregularities at the optical edge will give rise to some degree of light scattering and consequent mixing of the narrow angle light emission attributable only to surface-bound fluorescent material and the broader angle emission attributable to both surface-bound fluorescent material and fluorescent material in solution. This inevitably degrades the signal quality and overall performance of optical assay techniques using FCFD's.

SUMMARY OF THE INVENTION

The present invention is based on the discovery that light scattering at the optical edge can be substantially reduced in a particularly simple and efficient manner if the optical edge is contacted with an index matching substance so as to avoid having an optical edge/air interface.

Thus according to one aspect of the invention there is provided a method of reducing scattering of light emerging from an optical edge of an optical waveguide wherein said optical edge is maintained in intimate contact with an index matching substance which itself also forms or intimately contacts a further optical component.

By "index matching substance" is meant a substance having a refractive index similar to that of the material of the optical waveguide, e.g. having a refractive index which is ±10% that of the waveguide. Since high index glass as normally used in the production of waveguides typically has a refractive index of about 1.5, index matching substances having a refractive index in the range 1.35–1.65 are particularly appropriate for such applications.

Intimate contact between the optical edge and the index matching substance may be achieved by, for example, selecting an index matching substance which is a liquid or gel, or by employing precursors for a substantially transparent solid which pliably moulds to the surface of the optical edge before subsequently setting or otherwise solidifying.

Suitable liquid index matching substances include those traditionally employed as immersion fluids in microscopy, such as cedar oil and Canada balsam. Other liquids with appropriate refractive indices include silicones, ethyl alcohol, amyl alcohol, aniline, benzene, glycerol, paraffin oil and turpentine. Appropriate gels include, for example, silicone gels. Suitable precursors for solids include adhesives which may, for example, be selected from appropriate epoxy and acrylate systems, and optical cements as well as plastics materials (including thermoplastics) with appropriate refractive index, for example silane elastomers. Alternatively, readily meltable solids of appropriate refractive index, e.g. naphthalene, may be applied in molten form and then allowed to cool and solidify.

The method of the invention may, for example, be effected by index matching the optical edge to a defined optically smooth component, such as an optical flat, which forms the first stage of an optical detector train. Index matching may, for example, be made to an optical structure as described in published application WO 90/15985, the contents of which are herein incorporated by reference.

In a preferred embodiment of the invention, one or more FCFD's are positioned in a disposable holder (advantageously of the radially extending type described in published patent application WO 90/11830. Such holders may if desired incorporate an optical component such as a lens to which the optical edge is matched. Holders so constructed and incorporating an index matching substance constitute a further feature of the invention.

BRIEF DESCRIPTIONS OF THE DRAWINGS

In the accompanying non-limitative drawings, which serve to illustrate the invention without in any way limiting the same:

DETAILED DESCRIPTION OF THE INVENTION

Figure 1:
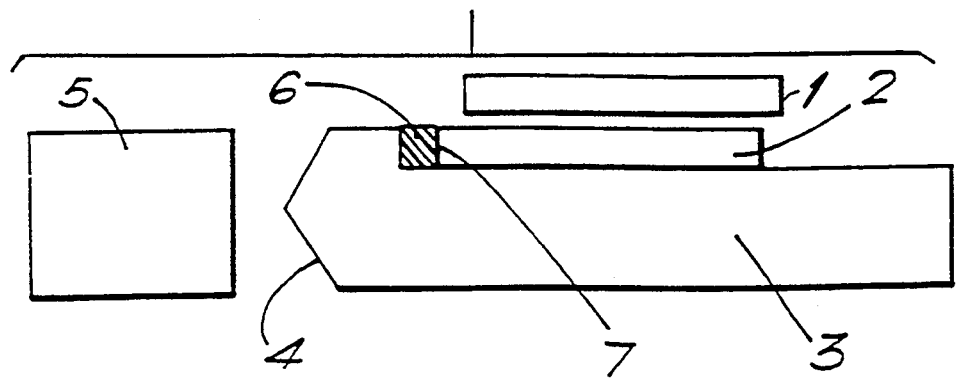
FIG. 1 is a schematic representation of a portion of a disposable holder incorporating an FCFD.

Referring to FIG. 1 in greater detail, upper glass plate 1 and optical wave guide 2 make up an FCFD mounted by means not shown in a disposable holder (e.g. produced by injection moulding), a part of which is shown as 3. It is preferred that the design of the holder is such that a plurality of FCFD cells radiate horizontally from a central vertical axis. That part of the edge of the holder closest to optical wave guide 2 is configured as a lens 4 associating with optical detector 5. Index matching substance 6, which is advantageously a solid such as an optical cement or appropriate plastic which during application pliably moulds to the optical edge 7 of waveguide 2, ensures that scattering of light between optical edge 7 and lens 4 is minimised.

Figure 2:
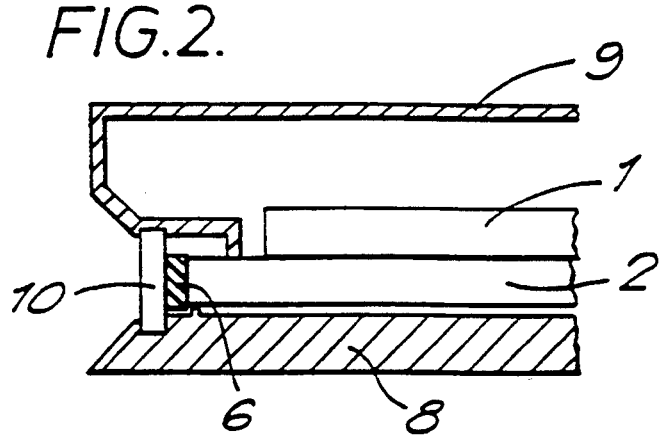
FIG. 2 is a vertical section through part of an alternative form of holder incorporating an FCFD.

In the configuration shown in FIG. 2 the upper glass plate 1 and optical waveguide 2 which constitute an FCFD are mounted in a holder comprising a base unit 8 and lid 9. A glass window 10 is mounted between said base unit 8 and lid 9 and is matched to the optical edge of wave guide 3 by means of index matching substance 6.

For a better understanding of the invention the following non-limitative Example is provided by way of illustration:

EXAMPLE 1

Figure 3:
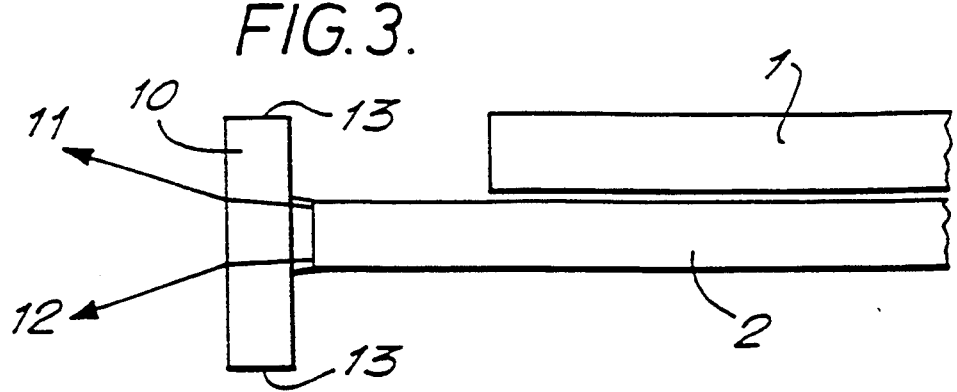
FIG. 3 is an enlarged partial view of the cross section of FIG. 2.

The configuration illustrated in FIG. 2 is employed. The glass window 10 is a flame polished microscope slide (e.g. as manufactured by Chance Propper Ltd., Smethwick, Warley, U. K.) which is cut to appropriate dimensions. As shown in FIG. 3, the height of the glass window is chosen so that those light rays 11, 12 which would normally (i.e. in the absence of index matching material) emerge from the waveguide at angles <47° to the axis thereof are refracted by the glass window without being reflected off its edge surface 13. For an FCFD with an optical edge of dimensions 1.1 mm by 10 mm, a suitable window is 4 mm by 10 mm with a thickness of 1.0 mm.

During assembly of the apparatus, the FCFD and glass window are placed in approximately moulded features in the (usually plastic) base unit 8 so that there is a small gap of approximately 0.1 mm between the optical edge 7 of the FCFD and the glass window. A drop of index matching material such as a UV-curable optical adhesive (e.g. Norland Optical Adhesive 81, Norland Products Inc., New Brunswick, U. S. A.) is then applied so that the small gap fills by capillary action and the adhesive is retained between the two components by surface tension. The adhesive is then cured by exposure to ultraviolet light at a wavelength of between 320 mm and 400 mm. The holder lid 9 is then attached to the base 8 and the whole may be stored for future use.

I claim:

1. An optical assay unit comprising a disposable holder, said holder comprising an optical component adapted to form the first stage of an optical detector train, a fluorescence capillary fill device FCFD mounted in said holder, said FCFD comprising a planar optical waveguide with an optical edge, and an index-matching substance intimately contacting said optical edge and said optical component.

2. An optical assay unit as claimed in claim 1 wherein the optical component comprises a lens or an optical fiat.

3. An optical assay unit as claimed in claim 1 or claim 2 comprising more than one FCFD and more than one optical component.

4. An optical assay unit as claimed in claim 1 wherein the index-matching substance is a liquid, a gel or a solid and is a precursor for a substantially transparent solid capable of being pliably moulded to the surface of the optical edge before setting or otherwise solidifying, said index-matching substance having a refractive index of between 1.35 and 1.65 after setting.

5. A method of reducing scattering of light emerging from an optical edge of an optical waveguide comprising maintaining said optical edge in intimate contact with an index-matching substance which intimately contacts a further optical component and wherein the optical waveguide forms part of a fluorescence capillary fill device, FCFD, positioned in a disposable holder comprising said optical component, said FCFD comprising an optical waveguide with an optical edge.

6. A kit for use in an optical assay comprising (a) one or more fluorescence capillary fill device(s), FCFD(s), each said FCFD comprising an optical waveguide with an optical edge (b) an index-matching substance and (c) a disposable holder adapted to receive said FCFD(s) and comprising one or more optical component(s) adapted to form the first stage of an optical detector train.

7. An optical assay unit as claimed in claim 2, wherein the index-matching substance is a liquid, a gel or a solid and is a precursor for a substantially transparent solid capable of being pliably moulded to the surface of the optical edge before setting or otherwise solidifying, said index-matching substance having a refractive index of between 1.35 and 1.65 after setting.

8. An optical assay unit as claimed in claim 3, wherein the index-matching substance is a liquid, a gel or a solid and is a precursor for a substantially transparent solid capable of being pliably moulded to the surface of the optical edge before setting or otherwise solidfying, said index-matching substance having a refractive index of between 1.35 and 1.65 after setting.

* * * * *